(12) United States Patent
Yan et al.

(10) Patent No.: US 9,937,280 B2
(45) Date of Patent: Apr. 10, 2018

(54) LUMINAL PROSTHESES AND METHODS FOR COATING THEREOF

(75) Inventors: John Yan, Los Gatos, CA (US); Howard Huang, Santa Clara, CA (US); Vinayak D. Bhat, Cupertino, CA (US)

(73) Assignee: Elixir Medical Corporation, Milpitas, CA (US)

( * ) Notice: Subject to any disclaimer, the term of this patent is extended or adjusted under 35 U.S.C. 154(b) by 2112 days.

(21) Appl. No.: 12/426,598

(22) Filed: Apr. 20, 2009

(65) Prior Publication Data

US 2009/0228094 A1 Sep. 10, 2009

Related U.S. Application Data

(63) Continuation-in-part of application No. PCT/US2007/081996, filed on Oct. 19, 2007.

(60) Provisional application No. 60/862,250, filed on Oct. 20, 2006.

(51) Int. Cl.
| | |
|---|---|
| *A61F 2/86* | (2013.01) |
| *A61L 27/34* | (2006.01) |
| *A61F 2/91* | (2013.01) |
| *A61F 2/915* | (2013.01) |
| *A61L 27/54* | (2006.01) |
| *A61L 29/08* | (2006.01) |
| *A61L 29/16* | (2006.01) |

(52) U.S. Cl.
CPC ............... *A61L 27/34* (2013.01); *A61F 2/91* (2013.01); *A61F 2/915* (2013.01); *A61L 27/54* (2013.01); *A61L 29/085* (2013.01); *A61L 29/16* (2013.01); *A61F 2002/91558* (2013.01); *A61F 2230/0054* (2013.01); *A61F 2250/0067* (2013.01); *A61L 2300/606* (2013.01); *A61L 2430/16* (2013.01)

(58) Field of Classification Search
USPC .......... 623/1.11, 1.12, 1.15, 1.42, 1.44, 1.45, 623/1.2; 424/423
See application file for complete search history.

(56) References Cited

U.S. PATENT DOCUMENTS

| | | | |
|---|---|---|---|
| 4,795,472 | A | 1/1989 | Crowninshield et al. |
| 6,120,847 | A | 9/2000 | Yang et al. |
| 6,153,252 | A | 11/2000 | Hossainy et al. |
| 6,224,894 | B1 | 5/2001 | Jamiolkowski et al. |
| 6,592,895 | B2 | 7/2003 | Lang et al. |

(Continued)

FOREIGN PATENT DOCUMENTS

| | | | |
|---|---|---|---|
| EP | A-0 875 218 | * | 4/1998 |
| WO | WO 96/02331 A1 | | 2/1996 |

OTHER PUBLICATIONS

International Search Report and Written Opinion of PCT Application No. PCT/US2007/081996, dated Jun. 10, 2008, 13 pages total.

*Primary Examiner* — Katrina Stransky
(74) *Attorney, Agent, or Firm* — Wilson Sonsini Goodrich & Rosati

(57) ABSTRACT

Luminal prostheses comprise scaffolds having coatings adhered to at least a portion of their outer surfaces. The surfaces are modified to enhance binding of the coatings. For example, the surfaces may be microblasted, laser treated, chemically etched, exposed to plasma, or exposed to a corona discharge, allowing a polymeric coating to adhere to the scaffold more tightly than in the absence of the surface modification. The coatings can be used to deliver therapeutic or other agents dispersed therein.

58 Claims, 11 Drawing Sheets

(56) References Cited

U.S. PATENT DOCUMENTS

| | | |
|---|---|---|
| 6,653,426 B2 | 11/2003 | Alvarado et al. |
| 6,709,379 B1 * | 3/2004 | Brandau et al. .................. 600/3 |
| 6,712,846 B1 | 3/2004 | Kraus et al. |
| 6,805,898 B1 * | 10/2004 | Wu et al. ...................... 427/2.25 |
| 6,824,559 B2 | 11/2004 | Michal |
| 6,855,770 B2 | 2/2005 | Pinchuk et al. |
| 6,913,617 B1 | 7/2005 | Reiss |
| 6,918,929 B2 | 7/2005 | Udipi et al. |
| 6,984,393 B2 | 1/2006 | Amsden |
| 7,008,979 B2 | 3/2006 | Schottman et al. |
| 7,055,237 B2 | 6/2006 | Thomas |
| 7,163,555 B2 | 1/2007 | Dinh |
| 7,232,573 B1 | 6/2007 | Ding |
| 2004/0156878 A1 | 8/2004 | Rezania et al. |
| 2005/0220839 A1 | 10/2005 | DeWitt et al. |
| 2005/0246009 A1 | 11/2005 | Toner et al. |
| 2005/0271700 A1 | 12/2005 | DesNoyer et al. |
| 2006/0009837 A1 | 1/2006 | Burgermeiste et al. |
| 2006/0067908 A1 | 3/2006 | Ding |
| 2006/0083772 A1 | 4/2006 | DeWitt et al. |
| 2006/0093771 A1 | 5/2006 | Rypacek et al. |
| 2006/0111546 A1 | 5/2006 | Pacetti et al. |
| 2006/0178721 A1 | 8/2006 | Durcan et al. |
| 2006/0198868 A1 | 9/2006 | DeWitt et al. |
| 2006/0212106 A1 | 9/2006 | Weber et al. |
| 2006/0257355 A1 | 11/2006 | Stewart et al. |
| 2006/0282166 A1 | 12/2006 | Molz et al. |
| 2007/0003592 A1 | 1/2007 | Hissink |
| 2007/0073016 A1 | 3/2007 | Alvarado et al. |
| 2007/0106371 A1 | 5/2007 | Datta et al. |
| 2007/0123973 A1 | 5/2007 | Roth et al. |
| 2007/0168012 A1 | 7/2007 | Ragheb et al. |
| 2007/0185569 A1 | 8/2007 | Hahn |
| 2007/0207184 A1 | 9/2007 | Ruane et al. |

* cited by examiner

LUMINAL PROSTHESES AND METHODS FOR COATING THEREOF

CROSS-REFERENCES TO RELATED APPLICATIONS

The present application is a continuation-in-part of U.S. Patent Application No. PCT/US07/81996 filed Oct. 19, 2007, which claims priority to U.S. Provisional Patent Application No. 60/862,250 filed Oct. 20, 2006, the disclosures of which are incorporated herein by reference.

BACKGROUND OF THE INVENTION

1. Field of the Invention

The present invention relates generally to medical devices and methods for their preparation. More particularly, the present invention relates to luminal prostheses having polymer coatings and methods for their preparation.

Luminal prostheses are used for maintaining patency in various body lumens, most notably in the vasculature and the ureter. The most common form of luminal prosthesis is referred to as a "stent," which is a generally tubular-shaped scaffold which is deployed to hold open or reinforce a segment of a body lumen. Stents are most commonly used in the vasculature where they are deployed in the coronary arteries, the carotid artery, the femoral artery, as well as in the peripheral arterial and venous vasculature. Stents and other luminal prostheses, however, also find use for treating aortic aneurysms, thoracic aneurysms, for supporting bioprosthetic valves, and for other purposes.

Stents are typically delivered to a target region within a body lumen using a catheter. Balloon-expandable stents are commonly mounted on a balloon catheter, navigated to the target region, and expanded by inflating the balloon. Self-expanding stents are most often delivered to a target region while constrained in a sheath or other tubular member. Once they reach the target region, the constraint can be removed and the stent will expand and deploy within the body lumen.

Stents and other luminal prostheses may also be modified to carry and elute drugs and pharmaceutical agents within a body lumen for a variety of purposes. Within the vasculature, the drugs and pharmaceutical agents are typically intended to reduce tissue inflammation, restenosis, or thrombosis, and/or to promote healing and biocompatibility of the device. Of particular interest to the present invention, drugs and other pharmaceutical agents are often eluted from a polymer matrix which has been coated over at least a portion of the stent surface. To be effective, the polymer should be able to accommodate stent preparation and processing as well as subsequent expansion within the vasculature or other body lumen. In particular, the coatings should suffer minimal or no cracking or smearing which can result from deformation and strain as the stent is crimped, expanded, or otherwise deformed during processing of delivery.

For these reasons, it would be desirable to provide improved coated prostheses, catheters for delivering such coated prostheses, and methods for fabricating such coated prostheses. In particular, the coatings on the prostheses should resist cracking and smearing during fabrication, preparation, and delivery to a targeted body lumen. The delivery catheters should further help reduce cracking and smearing during delivery. Finally, the fabrication methods should apply the coatings to the prostheses in a manner which promotes coatings which resist cracking and smearing. At least some of these objectives will be met by the inventions described below.

2. Description of the Background Art

The following U.S. patents and printed publications describe luminal prostheses and other implantable devices having polymer and other coatings for drug delivery and other purposes: U.S. Pat. Nos. 7,232,573; 7,163,555; 7,055,237; 7,008,979; 6,984,393; 6,918,929; 6,855,770; 6,824,559; 6,712,846; 6,653,426; 6,592,895; 6,653,426; 6,224,894; 6,153,252; and 6,120,847; and U.S. Publication Nos. 2007/0207184; 2007/0185569; 2007/0168012; 2007/0123973; 2007/0106371; 2007/0073016; 2007/0003592; 2006/0282166; 2006/0257355; 2006/0212106; 2006/0198868; 2006/0093771; 2006/0067908; and 2005/0271700.

SUMMARY OF THE INVENTION

The present invention provides luminal prostheses, catheter assemblies for delivering such prostheses, and methods for fabricating such prostheses. The luminal prostheses comprise a scaffold having a modified surface region which has a coating comprising a material which interacts with the modified surface region to provide an adherence of the coating to the surface greater than an adherence in the absence of the surface modification. The luminal prostheses comprise a scaffold having a modified surface region which has a coating comprising a material which softens in a physiologic environment and interacts with the modified surface region to provide an adherence of the coating to the surface greater than an adherence in the absence of the surface modification. The coating will typically comprise a polymer, as discussed below, but could also comprise proteins, peptides, extracellular matrix, metals, metal alloys, ceramics, and the like, and will often carry a therapeutic or other agent dispersed, distributed within the coating, or adjacent to the coating and intended to be released from the coating in a physiologic environment.

The scaffold will typically be in the form of a luminal stent, more typically being a stent intended for implantation within a patient's vasculature for treating regions of coronary artery or other vascular disease. Most commonly, the stents will be formed from a metal. Metal stents may either be balloon-expandable or self-expanding. The most common balloon-expandable stents are formed from stainless steel or cobalt-chromium alloys. Self-expanding stents are most commonly formed from nickel-titanium alloys or, in some cases, spring stainless steels. In addition to metal stents, the scaffolds of the present invention may be formed from polymeric materials, including both balloon-expandable (malleable) polymers and resilient polymers which could be used for preparing self-expanding scaffolds. Particular examples of stent patterns and stent materials are provided hereinafter.

Preferred coating materials comprise polymers having a glass transition temperature below physiologic temperature (37° C.). Such polymers may be non-erodible or erodible (biodegradable within the vascular or other luminal environment). Suitable erodible or biodegradable polymers will typically have a molecular weight above 50 KDa, usually over 150 KDa, and often over 200 KDa. Such erodible or biodegradable coatings may have widely varying times for degrading. For example, it may be desirable to employ polymers which degrade relatively rapidly, for example over a time period of less than six months, often less than three months, and in preferred embodiments, less than one month. Biodegradable polymers suitable for use in the present invention include poly(alkene carbonate) polymers, copolymers of poly(lactide) and trimethylene carbonate, copolymers of poly(lactide) and poly(glycolide), and copolymers of poly(lactide) and polyethylene glycol family of polymers. A preferred biodegradable polymer is polyethylene carbonate (PEC) having a molecular weight of 150 KDa or greater, which will substantially degrade when present in the vascular environment in less than six months, often less than three months, and usually less than one month.

A second exemplary erodible polymer comprises a copolymer of poly-L-lactide and trimethylene carbonate (PLLA:TMC). The molar percentage of PLLA in PLLA:TMC can range from 50% PLLA to 95% PLLA. which polymer coating degrades substantially in less than 4 years, more preferably less than 2 years, most preferably less than 1 year.

In another embodiment, the erodible polymer coating comprises a copolymer of poly-L-lactide and poly glycolic acid (PLLA:GA). The molar percentage of PLLA in PLLA:GA can range from 50% PLLA to 95% PLLA.

In another embodiment, the erodible polymer coating comprises a copolymer of poly lactide and polyethylene glycol (PLA:PEG). The molar percentage of PLA in PLA:PEG can range from 50% PLA to 99% PLA, which polymer coating degrades in less than 2 years, more preferably less than 1 year, most preferably less than 9 months.

Exemplary non erodible polymer compositions include poly(alkyl methacrylate) polymers. In a preferred embodiment the polymer is a poly-n-butylmethacrylate (PBMA). The non erodible polymers typically have molecular weight greater than 500 KDa, and an exemplary PBMA stent coating has a molecular weight greater than 700 KDa.

The polymer materials described above will usually be present in a pure or neat formulation with few or no additives or other materials, except for the therapeutic or other agents which are being incorporated in and delivered by the polymer coating. In other instances, however, the polymers described above could be combined with other materials or polymers for purposes known in the art. Such additional materials include plasticizers, anti-oxidants, stabilizers, and the like.

The polymer or other coatings on the scaffold will typically have a thickness in the range from 0.1 µm to 100 µm, preferably from 1 µm to 50 µm, and more preferably from 3 µm to 10 µm. The amounts of polymer coating may range from a total of 10 µg to 5 mg, preferably from 25 µg to 1 mg, and more preferably from 100 mg to 500 mg.

The polymer coatings will typically include one or more therapeutic or other agents at a relatively high loading percentage. Typically, the therapeutic or other agent will be present within the polymer in an amount greater than 30% of the total coating weight (including both polymer and therapeutic agent), more preferably being greater than 60% of the total coating weight, and most preferably being 65% of the total coating weight or greater. As mentioned above, other materials could also be included within the polymer coating, although the total loading of non-polymer materials will desirably be kept within the weight percentages set forth above.

The loading of therapeutic or other agent contained within the polymer can range from 1 ng/cm$^2$ to 1000 µg/cm$^2$, preferably 1 µg/cm$^2$ to 500 µg/cm$^2$, more preferably 10 µg/2 to 400 µg/cm$^2$, based on the area of the scaffold. The therapeutic or other agent is released from the polymer coating at rates ranging from 1 ng/cm$^2$/day to 1000 µg/cm$^2$/day, preferably 1 µg/cm$^2$/day to 200 µg/cm$^2$/day, more preferably from 5 µg/cm$^2$/day to 100 µg/cm$^2$/day. The therapeutic agent uptake in the tissue adjacent to the polymer coated stent can range from 0.001 ng/gm tissue to 1000 µg/gm tissue, preferably 1 ng/gm tissue to 100 µg/gm tissue, more preferably 100 ng/gm tissue to 50 µg/gm tissue. The therapeutic agent is usually released substantially completely from the prosthesis over a time ranging from 1 day to 6 months, preferably from 1 week to 3 months, more preferably from 2 weeks to 6 weeks. Release of the therapeutic or other agent from a non-erodible stent will typically depend on the nature of the pore structure or other reservoir formed within the polymer matrix. In the case of erodible stents, the therapeutic or other agent may be similarly released through a network of pores or other reservoir structure prior to eroding of the polymer. In other cases, however, release of the therapeutic agent may occur at least partly as a result of the polymer eroding over time.

Exemplary therapeutic agents that may be carried in the polymeric coating include immunomodulators, anti-cancer, anti-proliferative, anti-inflammatory, antithrombotic, anti-platelet, antifungal, antidiabetic, antihyperlipidimia, antiangiogenic, angiogenic, antihypertensive, or other therapeutic classes of drugs or combination thereof.

For example, immunomodulators agents includes but not limited to rapamycin, everolimus, Novolimus, ABT 578, AP20840, AP23841, AP23573, CCI-779, deuterated rapamycin, TAFA93, tacrolimus, cyclosporine, TKB662, myriocin, their analogues, pro-drug, salts, or others or combination thereof.

Illustrative anticancer agents include acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, Bacillus calmette-guerin (BCG), Baker's Antifol (soluble), beta-2'-deoxythioguanosine, bisantrene HCl, bleomycin sulfate, busulfan, buthionine sulfoximine, BWA 773U82, BW 502U83.HCl, BW 7U85 mesylate, ceracemide, carbetimer, carboplatin, carmustine, chlorambucil, chloroquinoxaline-sulfonamide, chlorozotocin, chromomycin A3, cisplatin, cladribine, corticosteroids, *Corynebacterium parvum*, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflomithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol®, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6,4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of Bacillus calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, reveromycin, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, QP-2, epothilone D, epothilone C Taxol, such as, paclitaxel, docetaxel, ABJ879, patupilone, MN-029, BMS247550, ecteinascidins such as ET-743, tetrahydroisoquinoline alkaloid, sirolimus, actinomycin, methotrexate, antiopeptin, vincristine, mitomycin, 2-chlorodeoxyadenosine or others, antifungal agents such as caspofungin, farnesylated dibenzodiazepinone, ECO-4601, fluconazole, or others, angiogenesis drugs such as follistatin, leptin, midkine, angiogenin, angiopoietin-1, becaplermin, Regranex, anti-angiogenesis drugs such as canstatin, angiostatin, endostatin, retinoids, tumistatin, vasculostatin, angioarrestin, vasostatin, bevacizumab, prinomastat, or others, antidiabetic drugs such as metformin, hypertension drugs such as candesartan, diovan, diltiazem, atenolol, adalat or others, anti-ischemia drugs such as ranolazine, isosorbide dinitrate, or others.

Illustrative antiinflammatory agents include classic nonsteroidal anti-inflammatory drugs (NSAIDS), such as aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nambumetone (relafen), acetaminophen (Tylenol®), and mixtures thereof; COX-2 inhibitors, such as nimesulide, NS-398, flosulid, L-745337, celecoxib, rofecoxib, SC-57666, DuP-697, parecoxib sodium, JTE-522, valdecoxib, SC-58125, etoricoxib, RS-57067, L-748780, L-761066, APHS, etodolac, meloxicam, S-2474, and mixtures thereof; glucocorticoids, such as hydrocortisone, cortisone, prednisone, prednisolone, methylprednisolone, meprednisone, triamcinolone, paramethasone, fluprednisolone, betamethasone, dexamethasone, fludrocortisone, desoxycorticosterone, fluticasone propionate, piroxicam, celeoxib, mefenamic acid, tramadol, meloxicam, methyl prednisone, pseudpterosin, or others, hypercalcemia drugs such as zoledronic acid, alendronate or others, antithrombosis drugs like plavix, heparin, Arixtra and Fraxiparine or others or mixtures thereof.

Therapeutic agents also include analogues, prodrugs, derivatives, precursors, fragments, salts, or other modifications or variations of pharmaceutical agents listed above. In another embodiment, the coating contains endothelial cell adhesion and/or growth promoting agent such as peptides such as RGD peptide sequence, extracellular matrix such as heparin sulphates, chondroitin sulphate, proteins such as fibronectin, fibrinogen, albumin or others. In one embodiment, the coating is applied directly on the surface of the prosthesis. In another embodiment, the coating is distributed or dispersed within a polymer and/or therapeutic agent. In one embodiment, an endothelial cell adhesion and/or growth promoting agent is attached to the prosthesis. In another embodiment, the endothelial cell adhesion and/or growth promoting agent is released from the prosthesis after implantation over time. The agent can be released from the prosthesis over a period in the range from 6 hr to 7 days, preferably from 7 days to 30 days, most preferably from 30 days to 6 months. In another embodiment, the endothelial cell adhesion and/or growth promoting agent is applied as topcoat to the polymer and/or therapeutic agent. The coating thickness is less than 5 µm, preferably less than 1 µm, most preferably less than 0.1 µm. The coating can be sprayed, dip coated, brushed, dispensed or by other means.

The present invention also provides catheter assemblies comprising a catheter having an expandable polymeric balloon, typically located near a distal end of a catheter body. A luminal prosthesis is carried on the expandable balloon, and the prosthesis generally comprises a scaffold and a coating formed over a modified region in the scaffold, as described in detail above.

In yet another aspect of the present invention, a luminal scaffold may be coated with a material by modifying at least a portion of a surface region of the scaffold and coating the material over the modified surface region. The modification is performed in order to increase the adherence of the polymer coating, and the coating and the modified surface will interact to have an adherence greater than the adherence in the absence of the surface modification. The luminal scaffolds and exemplary polymers may be the same as described above in connection with the structure of the luminal prosthesis itself. The surface modification may be any one of a variety of treatments intended to promote the adhesion of polymer coatings on a targeted region of the scaffold surface. In particular, it is desired that the adhesion be sufficient to prevent or minimize coating from cracking or smearing during stent crimping during processing or expansion during deployment. Surface texturing is a preferred modification which can be achieved through various methods, including micro-blasting, laser treatment, chemical etching, plasma exposure, or corona exposure. The surface modifications may be complete, partial or selective to cover all or portions of the exposed surfaces of the scaffold.

As a particular example, a microblast modified surface may provide round, trenches, regular or irregular shaped features. The average feature size (maximum length, diameter, or width) can vary preferably from 50 nm to 50 µm, more preferable 1 µm to 10 µm, and most preferably 5 µm to 10 µm. The average depth of the features can vary preferably from 50 nm to 50 µm, more preferable 1 µm to 10 µm, and most preferably 5 µm to 10 µm. The average density of features is preferably 0.001 to 0.10 features per $\mu m^2$, more preferably 0.003 to 0.05 features per $\mu m^2$, and most preferably 0.005 to 0.02 features per $\mu m^2$. The average size of blasting media for micro-blasting is preferably 5 µm to 100 µm, more preferably between 20 µm to 50 µm. The type of blasting media can be made from aluminum oxide, glass, metal, or other known in the art.

The stent surface modification enables polymer coating composition containing high percentage of therapeutic agents to be crimped or expanded with minimal or no cracking or smearing. In one embodiment, the percentage of therapeutic agent in the polymer composition may equal to or greater than about 40%, preferably equal to or greater than 65%, and more preferably equal to or greater than about 80%, while still maintaining an adherence greater than in the absence of surface modification.

After the surface region of the scaffold has been modified as described above, the polymer will be applied, typically together with the therapeutic or other agent. The polymer and the therapeutic or other agent are usually dissolved in one or more solvents prior to applying the coating on the stent surface. Typically, the choice of solvents is based on the solubility of the polymer and therapeutic agent. The solvent is preferably selected to have additional properties which minimize or eliminate cracking or smearing or promote adhesion of the coating to the stent upon crimping or expansion.

Residual solvents in polymer coatings on a stent can adversely impact coating cracking or smearing. It has been found by the inventors herein that solvents with low boiling points, high evaporation rates, low viscosities and/or high vapor pressures minimize residual solvents in polymer coating. By properly choosing the solvent, the residual solvent in the polymer will be less than 10000 ppm, preferably less than 5000 ppm, and more preferably less than 1000 ppm after stent coating. The solvent used for dissolving the coating preferably has a relative evaporation rate of 10 or higher (as compared to a rate of 1 for n-butyl acetate). The solvent preferably will also have a boiling point of 60° C. or lower. Further, the solvent will preferably have a vapor pressure of 50 mmHg or higher at 20° C. Still further, the solvent will preferably have a viscosity of 1 cP or lower at 25° C.

A solvent with low surface tension with the stent material is preferred to increase wetting the stent surface with coating and increasing the adhesion of the coating to the modified surface of the stent. The solvent will preferably have a surface tension of less than 70 dyne/cm, preferably less than 50 dyne/cm, more preferably less than 30 dyne/cm.

An empirical formula devised by the inventors herein can be used to determine which solvent best meets the requirement for dissolving the coating into a solution and using the solution to apply the coating onto the stent with a minimum residual solvent. The coating solvent index is calculated using the following formula:

$$\text{Coating Solvent Index Value} = \frac{\text{Evaporation Rate} \times \text{Vapor Pressure}}{\text{Boiling Point} \times \text{Viscosity} \times \text{Surface Tension}}$$

The properties and index of some typical solvents are provided in Table 1 below.

TABLE 1

| Chemical Name | Evaporation Rate (n-BuAc = 1) | Boiling Point @ 760 mmHg (° C.) | Vapor Pressure @ 20° C./ 68° F. (mmHg) | Viscosity (cP or mPa·s @ 25° C.) | Surface Tension (dynes/cm @ 25° C./77° F.) | Coating Solvent Index (Evap × Vapor/(BP × Visc × Surf Ten) |
|---|---|---|---|---|---|---|
| Diethylene glycol butyl ether acetate | 0.2 | 242 | 0.01 | 3.2 | 30 | 0.00 |
| Tripropylene glycol methyl ether | 0.2 | 236 | 0.03 | 6.0 | 29 | 0.00 |
| Tripropylene glycol normal butyl ether | 1 | 274 | 0.01 | 8.0 | 30 | 0.00 |
| Diethylene glycol butyl ether | 0.3 | 230 | 0.06 | 4.7 | 30 | 0.00 |
| Dipropylene glycol normal butyl ether | 1 | 229 | 0.02 | 4.8 | 29 | 0.00 |
| Propylene carbonate | 0.5 | 242 | 0.03 | 2.4 | 41 | 0.00 |
| N-methyl-2-pyrrolidone | 0.03 | 202 | 0.29 | 1.7 | 40 | 0.00 |
| Dipropylene glycol normal propyl ether | 1.3 | 212 | 0.05 | 4.4 | 26 | 0.00 |
| Dipropylene glycol methyl ether acetate | 1 | 200 | 0.05 | 2.2 | 28 | 0.00 |
| Ethylene glycol butyl ether acetate | 3 | 190 | 0.02 | 1.8 | 30 | 0.00 |
| Diethylene glycol ethyl ether | 2 | 198 | 0.12 | 4.5 | 32 | 0.00 |
| Diethylene glycol methyl ether | 2 | 194 | 0.2 | 3.9 | 35 | 0.00 |
| Dipropylene glycol methyl ether | 2 | 180 | 0.17 | 4.0 | 28 | 0.00 |
| Ethylene glycol butyl ether | 6 | 169 | 0.6 | 6.4 | 27 | 0.00 |
| Propylene glycol normal butyl ether | 7 | 170 | 0.62 | 3.5 | 26 | 0.00 |
| Propylene glycol methyl ether propionate | 19 | 157 | 0.9 | 1.1 | 34 | 0.00 |
| Propylene glycol normal propyl ether | 22 | 150 | 1.7 | 2.3 | 27 | 0.00 |
| Propylene glycol tertiary butyl ether | 30 | 151 | 2.81 | 4.0 | 24 | 0.01 |
| Isopropanol | 1.7 | 80 | 32 | 2.86 | 23 | 0.01 |
| Propylene glycol methyl ether acetate | 34 | 140 | 2.8 | 1.1 | 27 | 0.02 |
| Propylene glycol ethyl ether | 44 | 132 | 10 | 1.8 | 30 | 0.06 |
| Propylene glycol methyl ether | 70 | 120 | 8.1 | 2.0 | 27 | 0.09 |
| Methanol | 3.5 | 65 | 97 | 0.59 | 23 | 0.38 |
| Tertiary butyl alcohol | 95 | 82 | 31 | 3.3 | 20 | 0.54 |
| Tetrahydrofuran | 8 | 66 | 129 | 0.5 | 26 | 1.20 |
| Chloroform | 11.6 | 62 | 142 | 0.542 | 27 | 1.82 |
| Acetone | 5.6 | 56 | 184.5 | 0.32 | 25 | 2.31 |
| Diethylamine | 6.9 | 56 | 195 | 0.34 | 20 | 3.53 |
| Ethanol | 170 | 78 | 43 | 1.1 | 22 | 3.87 |
| Tertiary butyl acetate | 280 | 98 | 31 | 1 | 22 | 4.03 |
| Diclholormethane | 27.5 | 40 | 350 | 0.44 | 27 | 20.25 |

TABLE 1-continued

| Chemical Name | Evaporation Rate (n-BuAc = 1) | Boiling Point @ 760 mmHg (° C.) | Vapor Pressure @ 20° C./ 68° F. (mmHg) | Viscosity (cP or mPa · s @ 25° C.) | Surface Tension (dynes/cm @ 25° C./77° F.) | Coating Solvent Index (Evap × Vapor/(BP × Visc × Surf Ten) |
|---|---|---|---|---|---|---|
| Diethyl ether | 37.5 | 35 | 442 | 0.22 | 72.8 | 29.57 |
| Trichlorofluormethane | 63 | 24 | 803 | 0.43 | 18 | 272.34 |
| Methyl tertiary butyl ether | 814 | 55 | 204 | 0.3 | 19 | 529.68 |

The invention claims the use of a solvent with coating solvent index greater than 1, preferably greater than 10 and more preferably greater than 20.

After the luminal prosthesis has been prepared as described above, it will be loaded onto a delivery catheter. In the case of balloon-expandable prostheses, the balloon catheter will have an inflatable balloon, typically formed from a polymer, more typically a non-distensible polymer. The scaffold of the prosthesis will typically be crimp mounted on the balloon, and the stent and balloon thereafter placed in a polymer sheath and heated under high pressure. Such conventional heat treatment helps embed the scaffold into the delivery balloon with portions of the balloon "pillowing" into the interstices between the stent elements. As the heat setting has previously had a tendency to cause cracking or smearing in the polymeric coatings, it has been found that using balloons having a glass transition temperature lower than that of the coating polymer allows heat treatment at temperatures below those which would adversely impact the coating polymer material.

In yet another aspect of the present invention, a particular scaffold structure that is designed to minimize surface stresses during crimping and expansion is provided. The luminal scaffold comprises a plurality of axially joined serpentine rings having struts joined by crowns. The crowns on opposed adjacent rings are connected by straight connector links, where the connectors between successive pairs of adjacent rings are angled in opposite directions relative to an axial direction. In preferred embodiments, the connectors are disposed at angles in the range from 40° to 60° relative to the axial direction. The scaffold typically includes from six to 12 crowns, and from two to four diametrically opposed connectors between each pair of adjacent rings. The connectors usually have a length in the range from about 0.025 mm to 2.5 mm, and the crowns are rotationally offset in the range from 5° to 75° and axially separated by a distance in the range from 0.25 mm to 0.1 mm. Typically, the width and/or thickness of the connectors is less than the width and/or thickness of the crowns. In this way, the crowns will usually have a strain of 50% or less at the maximum radial expansion of the scaffold.

DETAILED DESCRIPTION OF THE INVENTION

Figure 1:
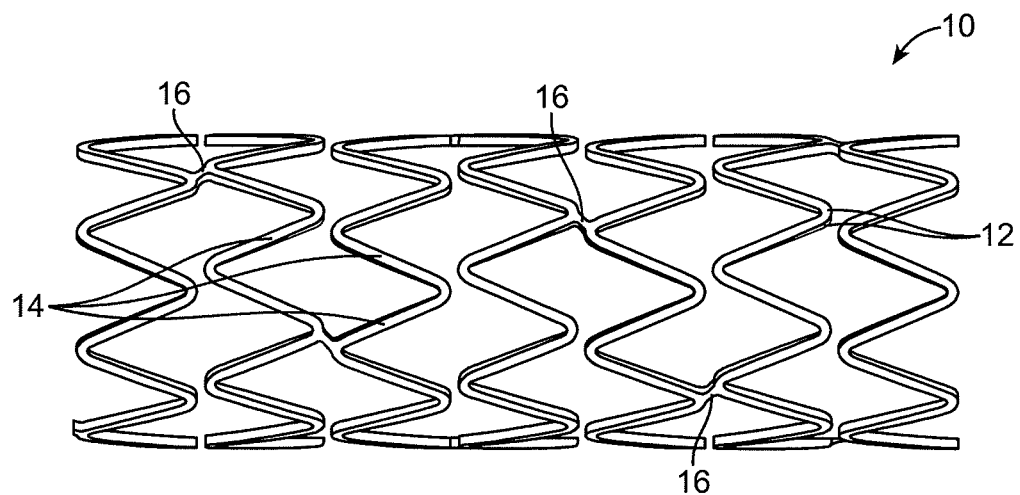
FIGS. 1, 1A and 2 illustrate an exemplary scaffold structure constructed in accordance with the principles of the present invention, with the stent and a catheter shown in FIG. 1A.
Figure 2:
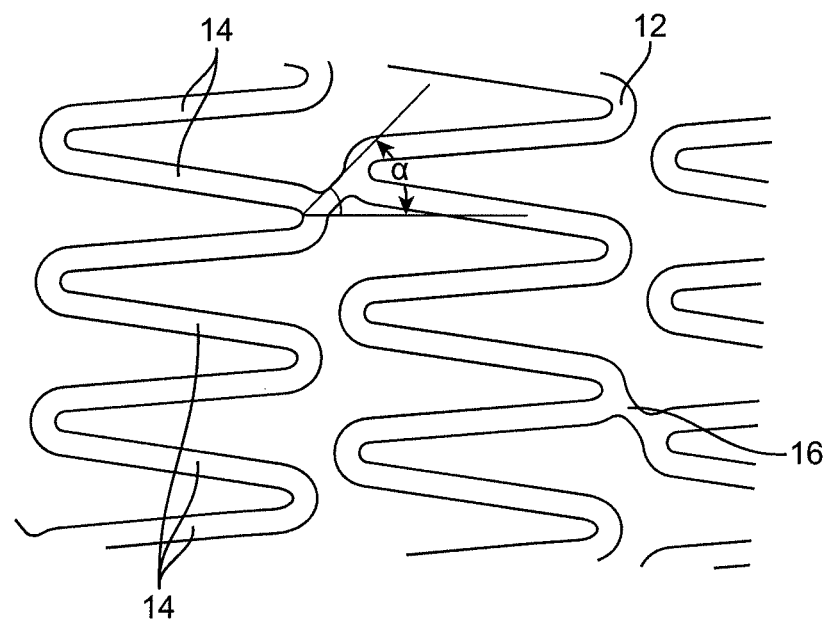

An exemplary vascular scaffold that is designed to minimize stress, cracking, or smearing of a coating is illustrated in FIGS. 1 and 2. The base structure of the scaffold is a lattice-like framework formed from a series of interconnected crowns 12 and struts 14 forming serpentine rings which are unit building blocks to form longer structures. Links 16 between rings affect the flexibility of the scaffold. Links 16 between rings are usually connected at the outside tips of the crowns 12 slightly offset from the centerline or peak of the crown, and oriented such that the next ring is offset from the previous ring allowing the crowns to avoid contact with each other as the stent is flexed. This amount of offset is determined by the take-off angle. The invention claims take-off angle α of the link to be between 30° and 60°, more preferably between 45° and 55°, as shown in FIG. 2.

Figure 1A:
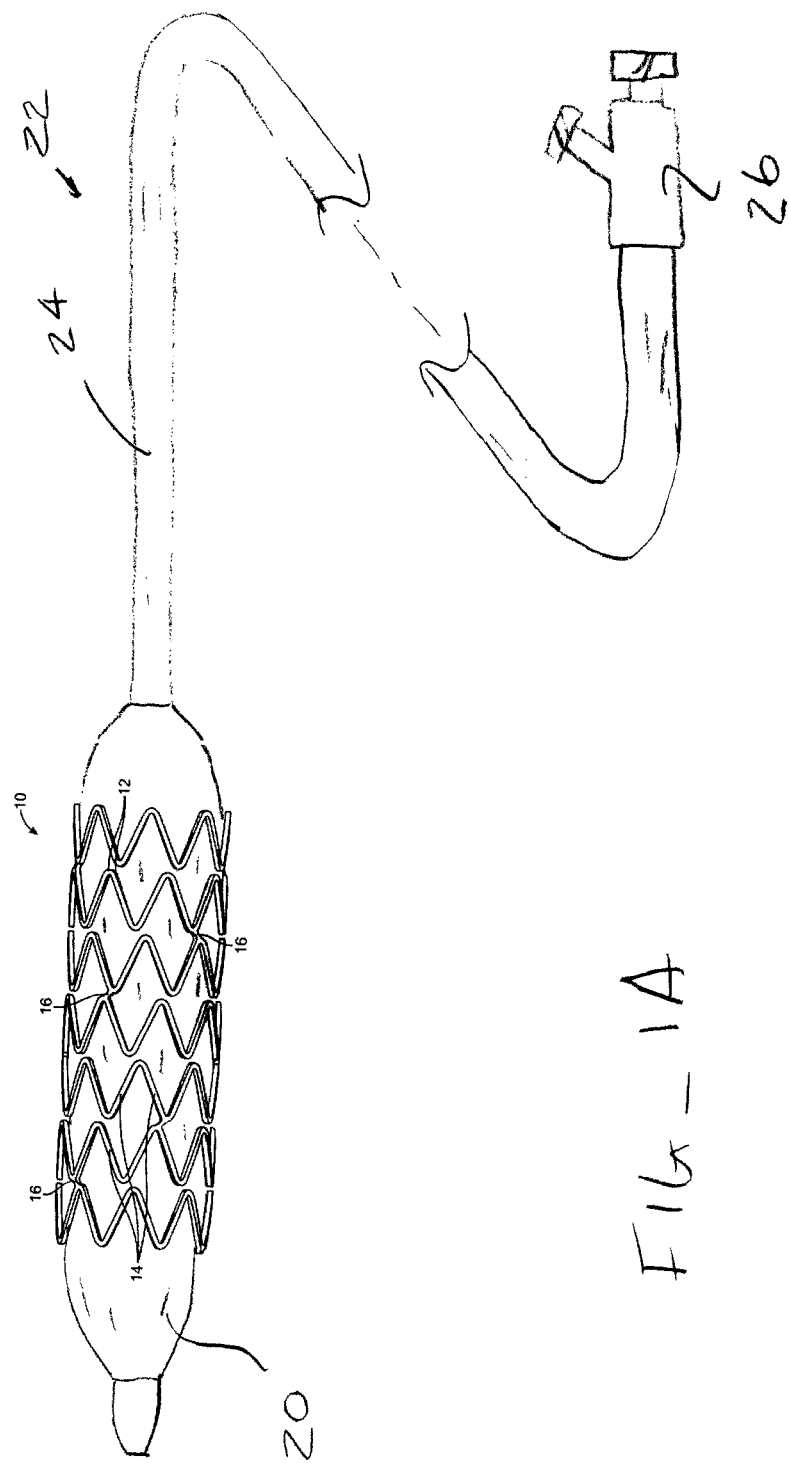

FIG. 1 illustrates the preferred embodiment in the expanded state with two connectors 16 and eight crowns 12 that provide flexibility and sidebranch access. The rings are slightly offset to avoid crown-to-crown contact to minimize strut-to-strut contact during crimping and flexion while maintaining sufficient scaffolding upon expansion. FIG. 2 illustrates how the connectors are joined to the crowns slightly offset from the peak of the crown 12 at a take-off angle of 50.degree. and alternate in direction from ring to ring to minimize uneven expansion. The stent 10 is shown on a balloon 20 of a balloon catheter 22 having a catheter body 24 and a proximal inflation hub 26, in FIG. 1A.

The link length and shape can also influence the suitability of the scaffold as a coating platform. The link shape is preferably straight to avoid interference with crowns. Also, the link length is selected to provide the minimum gap necessary to avoid interference contact between crowns during crimping and flexing, usually being from 0.025 mm to 2.5 mm. A longer link between rings will result in a greater gap between rings in the crimped state. The axial gap between rings or crowns of a crimped stent ranges from of 0.025 mm to 0.5 mm, preferably between 0.05 mm and 0.1 mm and more preferably 0.1 mm and 0.05 mm.

Another aspect of the present invention is to minimize the number of links to promote flexibility of the stent and provide adequate side branch access. The number of links can vary depending on the number of crowns of the stent. The number of links can be a multiple of the number of crowns to minimize uneven expansion. For example, nine crown stent would have three links, an eight crown stent two or four links, etc. The greater the number of crowns, the higher the scaffolding or coverage is at a given expanded diameter. For example eight crown stent with two links will provide superior scaffolding versus a six crown stent with two links of similar crown design at a given diameter. In a preferred embodiment, a stent design for 2.5-4.5 mm diameter expansion with two to four links and six to 12 crowns. The preferred embodiment is a stent with two links and eight crowns to cover the entire diameter range with one stent pattern.

Another aspect of the present invention is to minimize the width of the links to improve flexibility of the stent. The invention claims the width of the link to be thinner than the strut width of the crowns. The preferred embodiment has a strut width of 0.1 mm with link widths ranging from 0.05 mm to 0.075 mm wide. Thinner struts may be used while maintaining a link width to strut width ratio of 50% to 90%.

Another aspect of the present invention is to design the number and shape of crowns such that upon crimping to the desired diameter or flexing, the crowns do not touch each other and damage the coating on the stent while provide sufficient scaffolding upon expansion. Fewer crowns typically allow for a smaller crimp diameter before contact between crowns. The shape of the crowns also influences the likelihood of contact between crowns; a U-shaped crown formed from a tight radius will take up less space than a key-hole shaped crown with a larger radius. The invention claims an eight U-shaped crown stent with two links with a crimp diameter of less than 0.1 mm.

Finite element methods are commonly used to predict the strain induced during crimping or expansion of the stent. Lower strains help to minimize or eliminate coating cracking or smearing during crimping or expansion. Different materials will cause a stent to expand differently and thus experience different peak strains at maximum diameter.

For example a 0.08 mm thick cobalt-chrome eight crown stent with above design in FIGS. 1 and 2 resulted in less than 25% strain at maximum expansion and resulted in no coating cracks. The invention claims stent geometry with less than 50% peak strain, preferably less than 30% peak strain, more preferably less than 25% peak strain.

Another aspect of the present invention is that upon expansion, the rings are neither aligned in-phase or out of phase, so that the cell geometry is designed to provide scaffolding and adequate side branch access. When the crown tips are aligned with each other tip-to-tip, scaffolding is not optimal. When the rings are in phase, side-branch access may be compromised. By offsetting the rings slightly, scaffolding can be optimized while also maintaining adequate side branch access.

Another aspect of the present invention is that the links 16 inclined relative to the axial direction are oriented in alternating directions along the length of the scaffold, such that expansion forces are balanced and the scaffold expands evenly. Uneven or unbalanced expansion can have undesired effects on coatings present on the surface of the scaffold, as localized high-strain areas are introduced. Balancing upon expansion can be characterized using finite element methods and measuring the opening of each crown. The deviation or coefficient of variance between crown openings should be minimized. By alternating the direction of the links along the length of the stent, the coefficient of variance between crown openings in the design of FIGS. 1 and 2 was reduced from 8% to 3%. The invention can achieve a coefficient of variance between crown openings to be less than 5%.

Struts that are too thin relative to the width of the strut may have a tendency to twist as the stent is expanded, causing the coating to crack or smear. The invention claims a ratio of strut thickness versus strut width to be 0.6 to 1.0. In another embodiment, the current stent designs have little or no twisting out of plane upon expansion.

The stent implant may be manufactured using various methods, such as chemical etching, chemical milling, laser cutting, stamping, EDM, water et cutting, bending of wire, injection molding, and welding.

The stent material may start as wire, drawn tubing, co-drawn tubing for multiple layer stent constructions, flat sheet, or other forms. The stent material itself may be considered permanent, such as 316L stainless steel, cobalt-chromium alloy (L-605, MP35N), elgiloy, nitinol alloy, platinum, palladium, tantalum, or other alloys and polymers. Alternatively, biodegradable materials may also be used, such as magnesium, zinc, or their alloys or polymers such as poly-L-lactic acid, polyglycolic acid, polycaprolactone, copolymers of polylactic acid and polyethylene glycol and others.

It can be appreciated that all the various inventions and embodiments included in this application can be used alone or in various combinations with each other.

Example 1: Stent Surface Texturing

Figure 3:
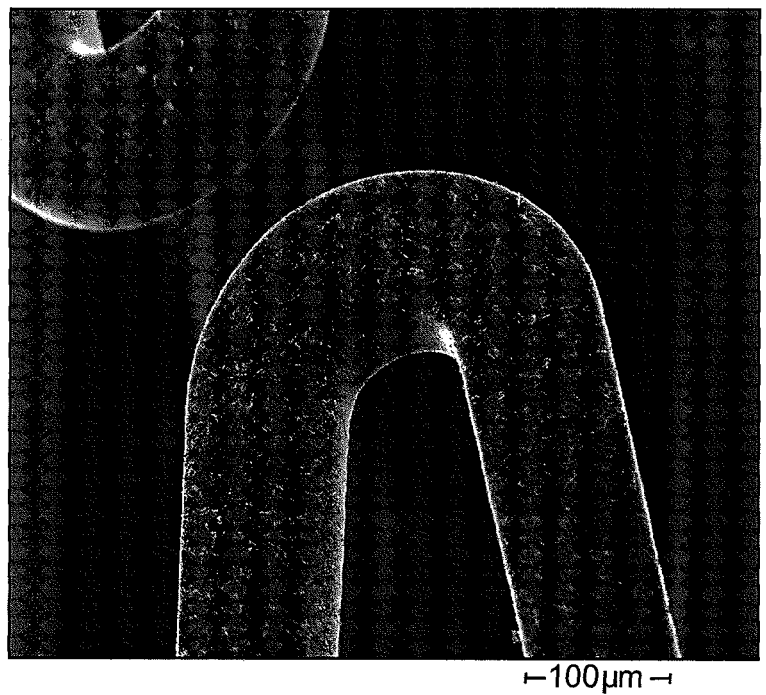
FIG. 3 is an SEM image of the outside of a luminal scaffold prepared as described in Example 1.

A 3×18 mm stent was put on a wire mandrel and rotated at 200 rpm. A micro-blaster with a 0.020" (0.5 mn) diameter nozzle was turned on such that 20 μm diameter media exits. The nozzle is placed 1 inch from the stent and allows it to traverse along the stent axially at a rate of 2 seconds per inch back and forth. It is allowed to microblast the stent for a total of 5 cycles. The stent direction is reversed and microblasting is repeated. The stent is then precrimped to a smaller inner diameter such as 0.036" (0.91 mn). It can be appreciated that the parameters used for surface texturing may vary. In this texturing process, the OD has higher average feature density than the ID and sidewall surfaces. FIG. 3 shows an SEM image of surface feature of a stent OD.

Example 2: Stent Surface Texturing

A 0.0500" (1.25 mm) diameter and 2" (5 cm) long hypotube is connected to the nozzle of a micro-blaster (Comco Inc). The hypotube is inserted into the lumen of a 3 mm×18 mm stent. The micro-blaster is turned on such that the 25 μm diameter media exits the end of the hypotube. The stent is then slowly removed from the hypotube which results in texturing the inner and at least some sidewall surfaces of the stent. The micro-blaster is turned off. The hypotube is again inserted into the lumen of the stent but in the reverse direction. The micro-blaster is turned on such that the 25 μm diameter media exits the end of the hypotube. The stent is then slowly removed from the hypotube which results in texturing the inner and at least some sidewall surfaces of the stent. The stent is then precrimped to a smaller inner diameter such as 0.036" (0.91 mn). It can be appreciated that the parameters used for surface texturing may vary.

Example 3: Stent Surface Texturing

Figure 4:
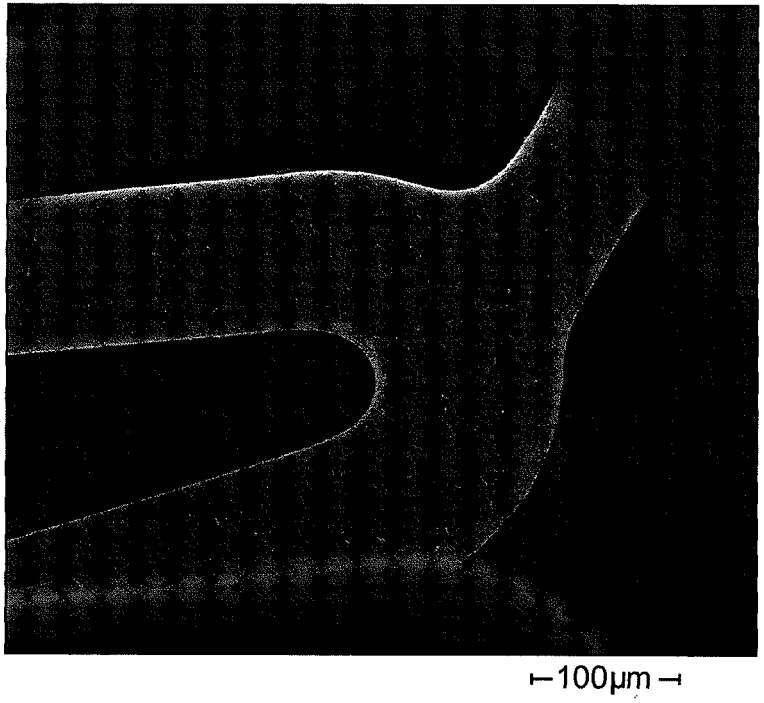
FIG. 4 is an SEM image showing the surface features of the scaffold prepared in Example 3.

The stent from example 2 undergoes further surface modification prior to precrimping to a smaller inner diameter. The stent is put on a wire mandrel and rotated at 200 rpm. A micro-blaster with a 0.020" (0.5 mn) diameter nozzle is turned on such that 20 μm diameter media exits. The nozzle is placed 1 inch from the stent and allows it to traverse along the stent axially at a rate of 2 seconds per inch back and forth. It is allowed to micro-blast the stent for a total of 5 cycles. The stent direction is reversed and microblasting is repeated. The stent is then precrimped to a smaller inner diameter such as 0.036" (0.91 mn). It can be appreciated that the parameters used for surface texturing may vary. FIG. 4 shows an SEM image of surface feature of a stent ID.

Example 4: Stent With PBMA Coating

A 0.011" (0.27 mn) wire mandrel is bent 360 degrees forming a loop at the apex. It is inserted into a surface treated stent from example 3 which was precrimped to 0.036" (0.91 mn) ID. The mandrel is then attached to the sample holding fixture of Sono-Tek Micromist™ ultrasonic coater such that the stent is rotated and moving back and forth beneath an ultrasonic nozzle. The coater has syringe pump that delivers a concentration of 40% macrocyclic lactone, such as Novolimus, with PBMA dissolved in dichloromethane solvent at a rate of 30 μl/min to the surface of an ultrasonic nozzle, resulting in their atomization. After the stent has linearly moved back and forth for a number of cycles, the coating process is terminated when the coating weight is approximately 450 μg PBMA:Novolimus. The stent is then placed in a vacuum for at 36 hrs to evacuate residual solvents to less than 50 ppm.

Example 5: Stent with Polyethylene Carbonate Coating

A 0.011" (0.27 mn) wire mandrel is bent 360 degrees forming a loop at the apex. It is inserted into a surface treated stent from example 1 which was precrimped to 0.036" (0.91 mn) ID. The mandrel is then attached to the sample holding fixture of Sono-Tek Micromist™ ultrasonic coater such that the stent is rotated and moving back and forth beneath an ultrasonic nozzle. The coater has syringe pump that delivers a concentration of 66% macrocyclic lactone with PEC dissolved in dichloromethane solvent at a rate of 30 μl/min to the surface of an ultrasonic nozzle, resulting in their atomization. After the stent has linearly moved back and forth for a number of cycles, the coating process is terminated when the coating weight is approximately 75 μg PEC:Macrocyclic lactone. The stent is then placed in a vacuum for at 36 hrs to evacuate residual solvents to less than 50 ppm.

Example 6: Stent with PLLA-TMC Coating

A 0.011" (0.27 mn) wire mandrel is bent 360 degrees forming a loop at the apex. It is inserted into a surface treated stent from example 1 which was precrimped to 0.036" (0.91 mn) ID. The mandrel is then attached to the sample holding fixture of Sono-Tek Micromist™ ultrasonic coater such that the stent is rotated and moving back and forth beneath an ultrasonic nozzle. The coater has syringe pump that delivers a concentration of 40% macrocyclic lactone (such as Novolimus) with PLLA-TMC dissolved in dichloromethane solvent at a rate of 30 μl/min to the surface of an ultrasonic nozzle, resulting in their atomization. After the stent has linearly moved back and forth for a number of cycles, the coating process is terminated when the coating weight is approximately 450 μg PLLA-TMC:Macrocyclic lactone. The stent is then placed in a vacuum for at 36 hrs to evacuate residual solvents to less than 50 ppm.

Example 7: Stent Crimp Mounting and Expansion

Figure 5:
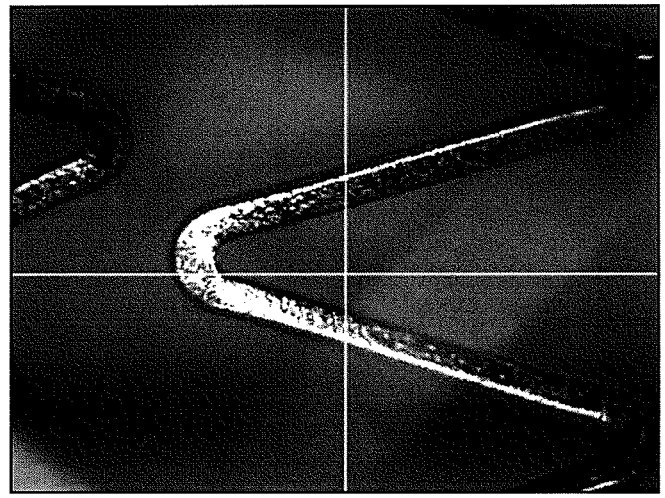
FIG. 5 is a light microscope image of the inside of the stent prepared in Example 5 after mounting and expansion as described in Example 7.
Figure 6:
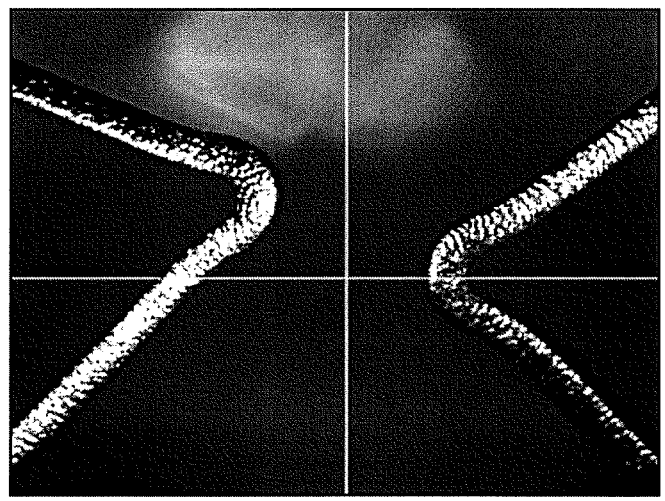
FIG. 6 is a light microscope image of the outside diameter of the stent described in Example 7.

The coated stent from either sample 4, 5, or 6 is inserted into a 0.046" (1.1 mn) inner diameter PTFE sheath. The folded nylon copolymer balloon on the distal end of a 20 mm long balloon stent delivery system is inserted into the stent lumen. The balloon is pressurized to 250 psi while the PTFE sheath surface is heated to about 35° C. above the Tg of the polymer coatings for about 30 seconds and then cooled. After cooling, the balloon may be depressurized. The PTFE sheath is removed from the stent, leaving a crimped stent on the balloon of the catheter. The stent delivery catheter may then be packaged and sterilized by ethylene oxide. The stent is expanded under physiological conditions with minimal to no cracking or smearing of the coating. FIGS. 5 and 6 show light microscopy images of ID and OD of a PEC coated stent after expansion.

Example 8: In Vivo Testing of PBMA Coated Stent and PEC Coated Stent

Tissue and blood compatibility of PBMA coated and PEC coated stents were evaluated in by comparing histomorphometry and pathology of the tissue around the stents in a porcine coronary artery model after 28 and 90 days of implantation. The stents were coated with PBMA (as in example 4) and PEC (as in example 5) but with polymer only without any drug content.

The nonatherosclerotic swine model was chosen as this model has been used extensively for stent and angioplasty studies resulting in a large volume of data on the vascular response properties and its correlation to human vascular response (Schwartz et al, Circulation. 2002; 106:1867-1873). The animals were housed and cared for in accordance the Guide for the Care and Use of Laboratory Animals as established by the National Research Council.

All animals were pretreated with aspirin 325 mg and clopidogel (75 mg) per oral beginning at least 3 days prior to the intervention and continuing for duration of the study. After induction of anesthesia, the left or right femoral artery was accessed using standard techniques and an arterial sheath was introduced and advanced into the artery.

Vessel angiography was performed under fluoroscopic guidance, a 7 Fr. guide catheter was inserted through the sheath and advanced to the appropriate location; intracoronary nitroglycerin was administered. A segment of coronary artery ranging from 2.25 to 4.0 mm mean lumen diameter was chosen and a 0.014" (0.35 mm) guidewire inserted. Quantitative Coronary Angiography (QCA) was performed to document the reference vessel diameter.

The appropriately sized stent was advanced to the deployment site. The balloon was inflated at a steady rate to a pressure sufficient to achieve a balloon to artery ratio of 1.1:1.0. Pressure was maintained for approximately 10 seconds. Angiography was performed to document post-procedural vessel patency and diameter.

Follow-up angiography was performed at the designated endpoint for each of the animals. Each angiogram was qualitatively evaluated for evidence of stent migration, lumen narrowing, stent apposition, presence of dissection or aneurysms, and flow characteristics. Upon completion of follow-up angiography, the animals were euthanized.

The hearts were harvested from each animal and the coronary arteries were perfused with 10% buffered formalin at 100 to 120 mm Hg. The hearts were immersed in 10% buffered formalin. Any myocardial lesions or unusual observations were reported.

Angiographic parameters measured or calculated included:
1. Marginal vessel (proximal and distal) mean lumen diameter (post-stent and final)
2. Mean lumen diameter of the target region (all angiograms)
3. Minimal lumen diameter (MLD) of the target region (post-stent and final only)
4. Diameter stenosis [1−(MLD/RVD)]×100%] where RVD is a calculation of the reference diameter at the position of the obstruction (measure obtained by a software-based iterative linear regression technique to generate an intrapolation of a projected vessel without the lesion) (final angiogram only).
5. Balloon to artery ratio [balloon/pre-stent mean luminal diameter]
6. Stent to artery ratio [post-stent/pre-stent mean luminal diameter]
7. Late loss ratio [MLD final-MLD post-stent]

Figure 7:
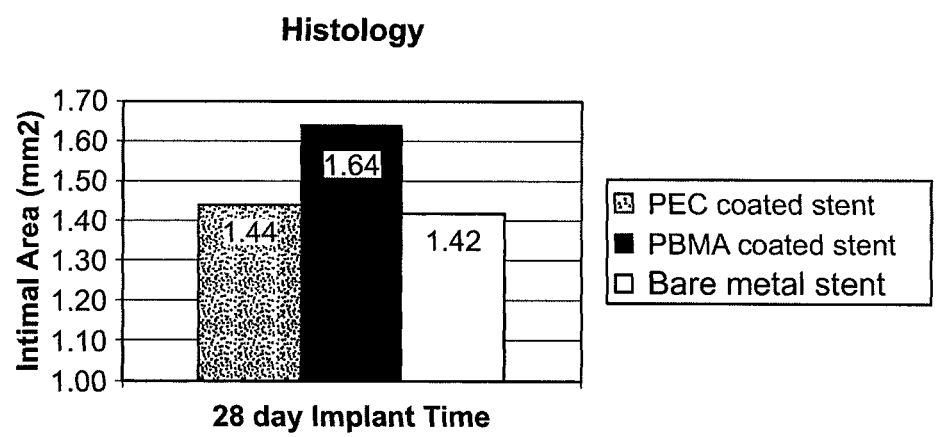
FIG. 7 is a chart comparing the neointimal area of stents coated with PEC and PBMA in comparison to a bare metal stent after 28 days of implantation in a porcine coronary artery model, as described in Example 8.
Figure 8:
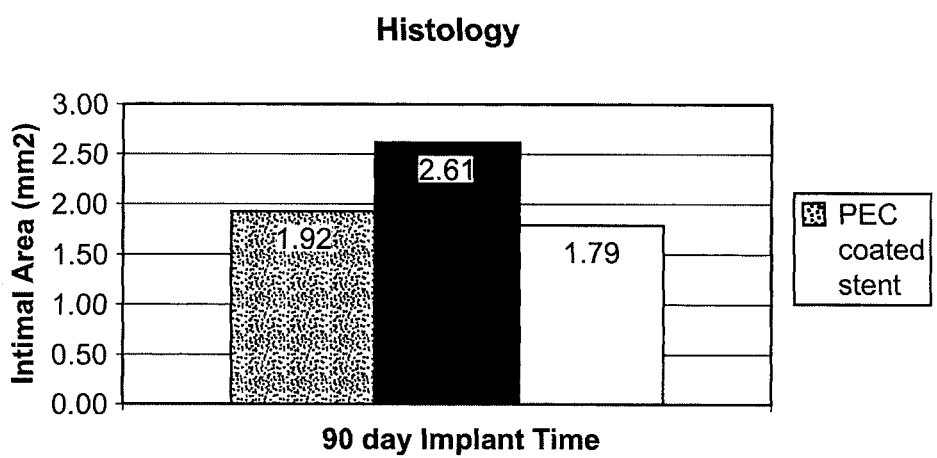
FIG. 8 is similar to FIG. 7, showing the results after 90 days of implantation.

All animal survived to the designated end point. There were no documented incidents of stent migration, stent malapposition, persistent dissection or evidence of aneurysm. At 28-days the three groups showed similar results in intimal area ($mm^2$) of 1.44±0.58 vs. 1.64±0.82 vs. 1.42±0.68 for PEC coated, PBMA coated and Bare Metal stent respectively (FIG. 7). Pathological examination for fibrin deposition, calcification and endothelialization showed comparable results across all stents. At 90-days the three groups showed similar results in intimal area ($mm^2$) of 1.92±0.8 vs. 2.61±0.7 vs. 1.79±0.9 for PEC coated, PBMA coated and Bare Metal stent respectively (FIG. 8). Pathological examination for fibrin deposition, calcification and endothelialization showed comparable results across all stents. PEC and PBMA coatings in this example showed comparable biocompatibility to bare metal stents in an in vivo model Example 9: In Vivo Testing of PEC Drug Coated Stent The efficacy of a PEC drug coated stent (as prepared above in Example 5) with 60-75 µg of PEC:macrocyclic lactone drug compound was evaluated by comparing 28±2 day, 90±5 day, and 180±5 day histomorphometric outcomes in porcine coronary arteries to rapamycin eluting stent system, Cypher™ coronary stent (Cordis Corporation) in the non-diseased porcine coronary artery model. The interventional procedure is as described in Example 8; for the 28-day implant stent implantation was conducted at a higher balloon:artery ratio of 1.3:1.0 and for the 90-day and 180-day implants, stent implantation was conducted at the lower balloon:artery ratio of 1.1:1.0.

Figure 9:
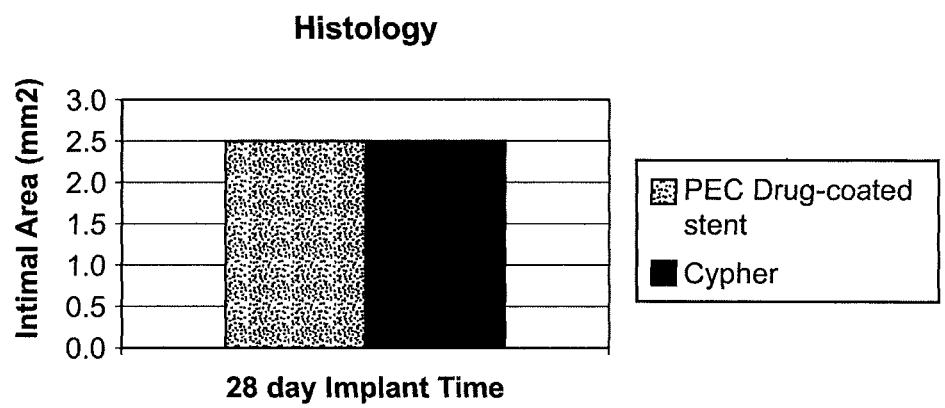
FIG. 9 compares the neointimal area achieved with PEC drug coated stents with that achieved in a Rapamycin eluting Cypher™ stent after 28 days of implantation in a porcine coronary artery model, as described in Example 9.

28-day Implant: All animal survived to the designated end point. There were no documented incidents of stent migration, stent malapposition, persistent dissection or evidence of aneurysm. The average intimal area ($mm^2$) for the PEC drug coated stent (approx. 2.5 µg/mm length drug dose) was 2.5±1.2 (n=15) as compared to the pooled Cypher™ stent data provided an average intimal area ($mm^2$) of 2.5±0.9 (n=40. (FIG. 9).

The PEC drug coated stents in this example when implanted in the porcine model for 28 days resulted in similar neointimal formation as the Cypher™ stent.

Figure 10:
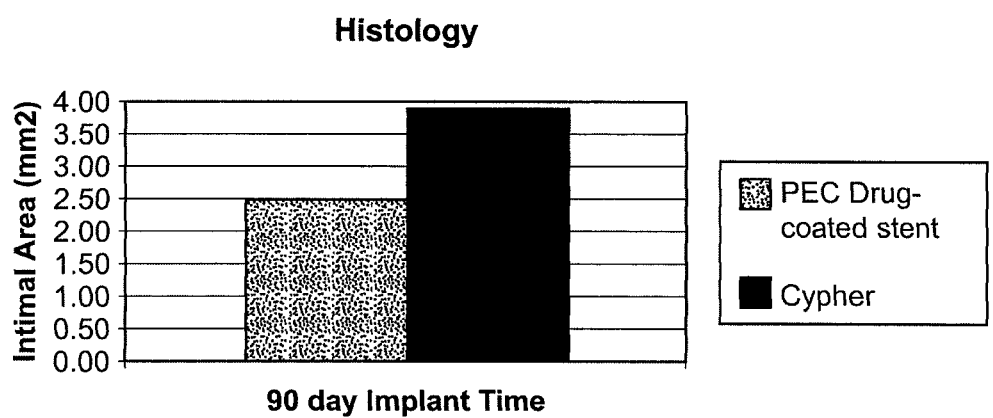
FIG. 10 is similar to FIG. 9 showing the results after 90 days of implantation.

90-day Implant: All animals survived to the designated end point. There were no documented incidents of stent migration, stent malapposition, persistent dissection or evidence of aneurysm. The average intimal area ($mm^2$) for the PEC drug coated stent (approx. 2.5 µg/mm length drug dose) was 2.50±0.9 (n=6) as compared to the implanted Cypher™ stent which provided an average intimal area ($mm^2$) of 2.3.9±2.2 (n=20). (FIG. 10)

The PEC drug coated stents in this example when implanted in the porcine model for 90 days resulted in similar neointimal formation as the Cypher™ stent.

Figure 11:
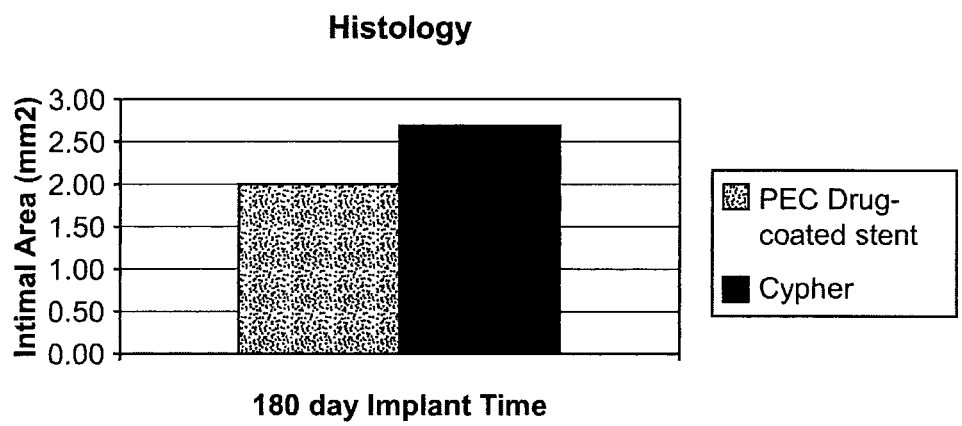
FIG. 11 compares the neointimal area achieved with PEC coated stents with that achieved by Rapamycin eluting Cypher™ stents after 180 days of implantation in a porcine coronary artery model.

180-day Implant: All but one animal survived to the designated end point. The animal that did not survive died at day 6 due to a thrombus formation caused by procedural issue of under dilation of a stent during implantation. There were no documented incidents of stent migration, stent malapposition, persistent dissection or evidence of aneurysm. The average intimal area ($mm^2$) for the PEC drug coated stent (approx. 4.4 µg/mm length drug dose) was 1.98±0.7 (n=2) as compared to the concurrently implanted Cypher™ stent provided an average intimal area ($mm^2$) of 2.70±1.15 (n=2). (FIG. 11)

The PEC drug coated stents in this example when implanted in the porcine model for 180 days resulted in similar neointimal formation as the Cypher™ stent.

Example 10: In Vivo Pharmacokinetics of PEC Drug Coated Stents

Pharmacokinetic evaluation of the PEC drug coated stent system from Example 9 was performed at 6 hours, 3 days and 28 days in the porcine coronary artery model.

The interventional procedures are similar to the in vivo angiographic study described in Example 8 up to stent implantation. The appropriately sized stent was advanced to the deployment site. The balloon was inflated at a steady rate to a pressure sufficient to achieve a balloon to artery ratio of 1:1. Pressure was maintained for approximately 10 seconds. Angiography was performed to document post-procedural vessel patency and diameter. A total of 9 stents (3 per time point) were implanted.

At the appropriate time point the animals were euthanized and the hearts excised. The stented segment including approximately 10 mm of vessel proximal and 10 mm distal to the stented section was excised. The proximal and distal sections were separated and stored in separate vials. The tissue surrounding the stent was carefully removed from stent and each place in separate vials. All were then frozen to −70° C. prior to being analyzed using high performance liquid chromatography (HPLC).

Figure 12:
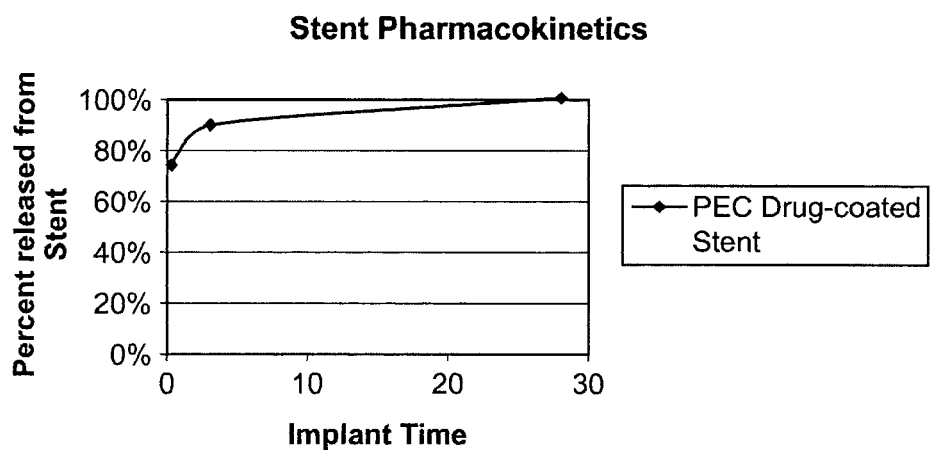
FIG. 12 is a graph illustrating the percentage of release of PEC from a coated stent over time in a porcine coronary artery model.
Figure 13:
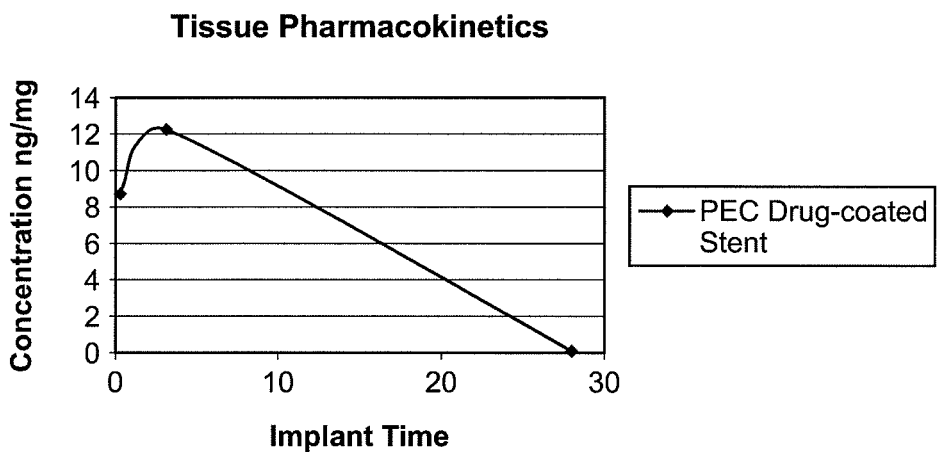
FIG. 13 is a graph depicting tissue concentration of PEC achieved at different time points in a porcine coronary artery model, as described in Example 10.

All animal survived to the designated end point. The stent and tissue pharmacokinetics for the PEC drug coated stent are presented in FIGS. 12 and 13.

The PEC drug coated stent, in this example, demonstrates the release profile of drug from the stent with approximately 90% of the drug released with in 7 days with drug tissue concentrations present over at least the same period.

Example 11: In Vivo Testing of PBMA Drug Coated Stent

The efficacy of a PBMA drug coated stent (as prepared above in Example 4) with 450 µg of PBMA:Novolimus drug compound was evaluated by comparing 28±2 day and 90±5 day histomorphometric outcomes in porcine coronary arteries to rapamycin eluting stent system, Cypher™ coronary stent (Cordis Corporation) in the non-diseased porcine coronary artery model. The interventional procedure is as described in Example 8 but with a higher balloon:artery ratio of 1.3:1.0 and for the 90-day implants, stent implantation was conducted at the lower balloon:artery ratio of 1.1:1.0.

Figure 14:
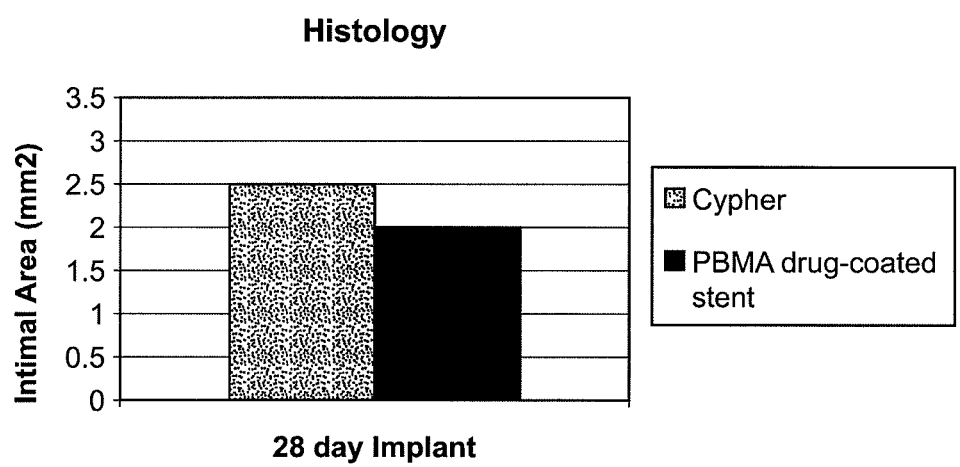
FIG. 14 compares the neointimal area achieved with a PBMA coated stent with that obtained with a Rapamycin eluting Cypher™ stent after 28 days of implantation in a porcine coronary artery model, as described in Example 11.

28-day Implant: All animal survived to the designated end point. There were no documented incidents of stent migration, stent malapposition, persistent dissection or evidence of aneurysm. Three outlying data points (total occlusion or near total occlusion) for the Cypher™ stent were excluded. The average intimal area (mm$^2$) for the PBMA drug coated stent (approx. 10 µg/mm length drug dose) was 2.0±0.5 (n=14) as compared to Cypher™ stent pooled data from this and previous studies with similar protocols which provided an average percent stenosis of 2.5±0.9 (n=40) for Cypher™ stents. (FIG. 14)

The PBMA drug coated stent in this example when implanted in the porcine model for 28 days resulted in similar neointimal formation as the Cypher™ stent.

Figure 15:
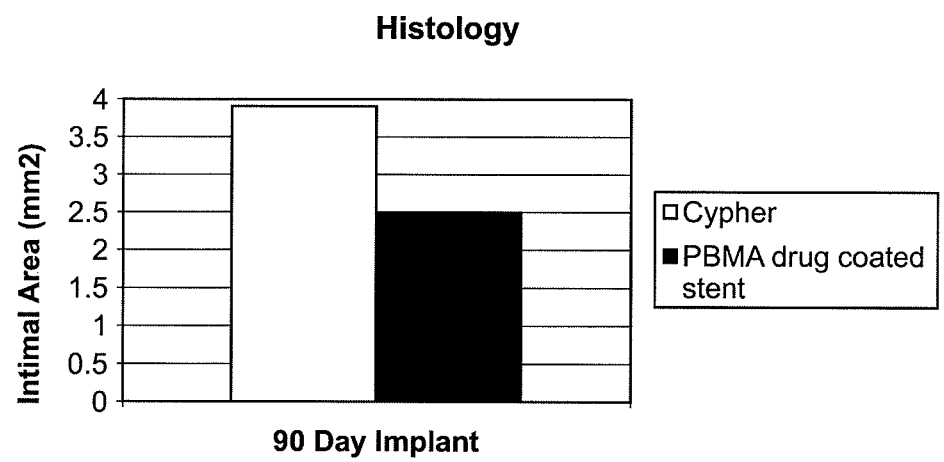
FIG. 15 is similar to FIG. 14, showing the results after 90 days of implantation.

90-day Implant: All animal survived to the designated end point. There were no documented incidents of stent migration, stent malapposition, persistent dissection or evidence of aneurysm. Three outlying data points (total occlusion or near total occlusion) for the Cypher™ stent were excluded. The average intimal area (mm$^2$) for the PBMA drug coated stent (approx. 10 µg/mm length drug dose) was 2.5±0.6 (n=6) as compared to Cypher™ stent pooled data from this and previous studies with similar protocols which provided an average percent stenosis of 3.9±2.2 (n=20) for Cypher™ stents. (FIG. 15)

The PBMA drug coated stent in this example when implanted in the porcine model for 90 days resulted in similar neointimal formation as the Cypher™ stent.

Example 12: In Vivo Pharmacokinetics of PBMA Drug Coated Stents

Figure 16:
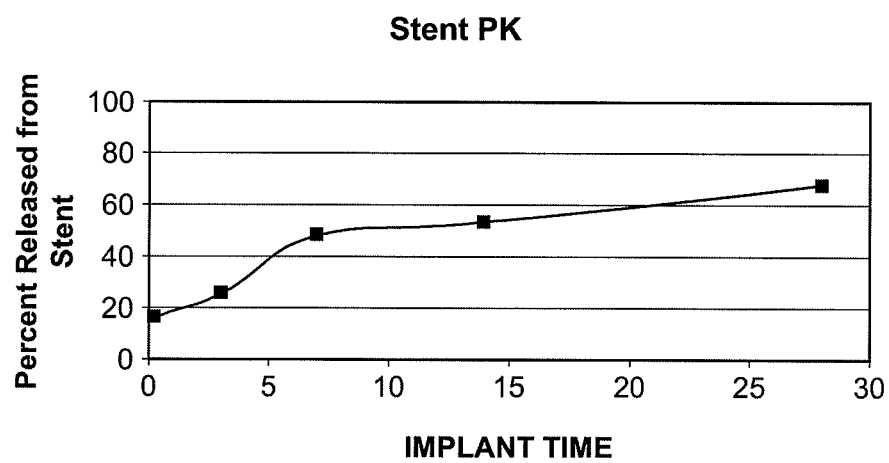
FIG. 16 is a graph illustrating the percentage of PBMA released from a coated stent in a porcine coronary artery model over time, as described in Example 11.
Figure 17:
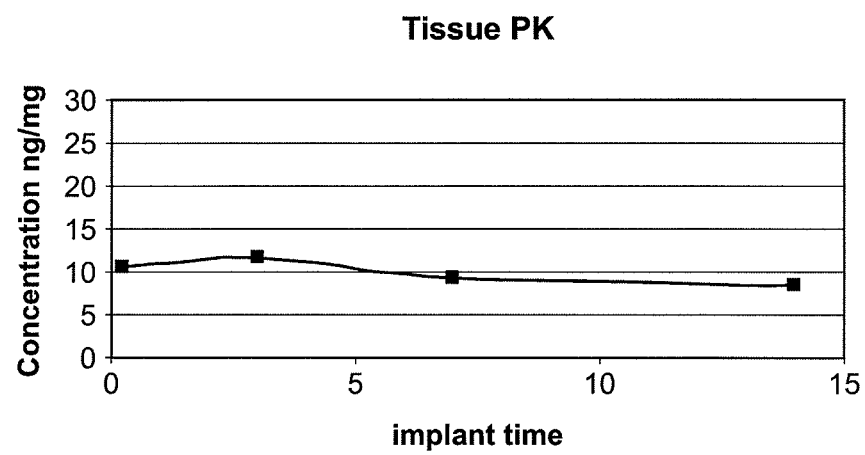
FIG. 17 is a graph showing the tissue concentration of PBMA released from a coated stent over time in a porcine coronary artery model, as described in Example 12.

Pharmacokinetic evaluation of the PBMA drug coated stent system from Example 11 was performed at 6 hours, 3 days and 28 days in the porcine coronary artery model The interventional procedures are similar to the in vivo angiographic study described in Example 10. All animal survived to the designated end point. The stent and tissue pharmacokinetics for PBMA drug coated stents FIGS. 16 and 17.

The PBMA drug coated stent, in this example demonstrates release of drug from the stent with approximately 50% of the drug released at 7 days and approximately 70% at 28 days with drug tissue concentrations present over at least a 14 day period.

Example 13: In Vivo Testing of PLLA-TMC Drug Coated Stent

The efficacy of a PLLA-TMC drug coated stent (as prepared above in Example 6) with 75 µg of PLLA-TMC drug compound was evaluated by comparing 28±2 day angiographic outcomes in porcine coronary arteries to rapamycin eluting stent system, Cypher™ coronary stent (Cordis Corporation) in the non-diseased porcine coronary artery model. The interventional procedure is as described in Example 8; for the 28-day implant stent implantation was conducted at a higher balloon:artery ratio of 1.3:1.0

Figure 18:
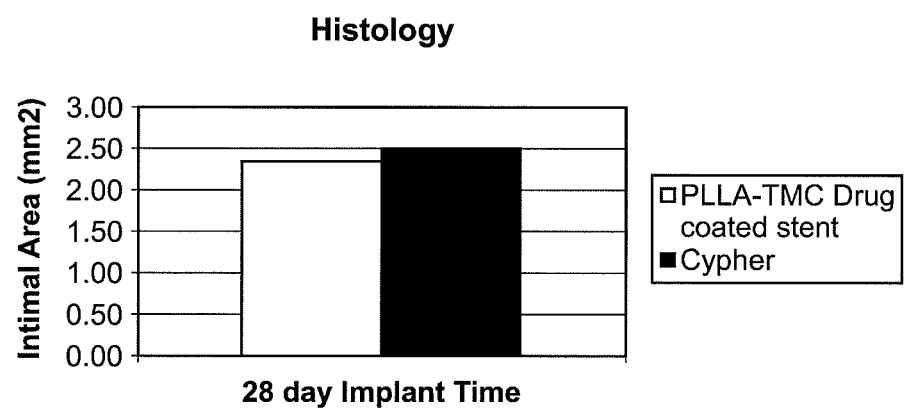
FIG. 18 compares the neointimal area achieved with a PLLA-TMC coated stent compared to a Rapamycin eluting Cypher™ stent after 28 days of implantation in a porcine coronary artery model, as described in Example 12.

All animal survived to the designated end point. There were no documented incidents of stent migration, stent malapposition, persistent dissection or evidence of aneurysm. The average intimal area (mm$^2$) for the PLLA-TMC drug coated stent (approx. 2.7 µg/mm length drug dose) was 2.3±0.9 (n=8) as compared to the Cypher™ stent provided an average intimal area (mm$^2$) of 2.5±0.9 (n=40). (FIG. 18)

The PEC drug coated stents in this example when implanted in the porcine model for 28 days resulted in similar neointimal formation as the Cypher™ stent.

Example 14: In Vivo Pharmacokinetics of PLLA-TMC Drug Coated Stents

Pharmacokinetic evaluation of the PEC drug coated stent system from Example 6 was performed at 6 hours, 3 days and 28 days in the porcine coronary artery model The interventional procedures are similar to the in vivo angiographic study described in Example 8 up to stent implantation. The appropriately sized stent was advanced to the deployment site. The balloon was inflated at a steady rate to a pressure sufficient to achieve a balloon to artery ratio of 1:1. Pressure was maintained for approximately 10 seconds. Angiography was performed to document post-procedural vessel patency and diameter. A total of 9 stents (3 per time point) were implanted.

At the appropriate time point the animals were euthanized and the hearts excised. The stented segment including approximately 10 mm of vessel proximal and 10 mm distal to the stented section was excised. The proximal and distal sections were separated and stored in separate vials. The tissue surrounding the stent was carefully removed from stent and each place in separate vials. All were then frozen to −70° C. prior to being analyzed using high performance liquid chromatography (HPLC).

Figure 19:
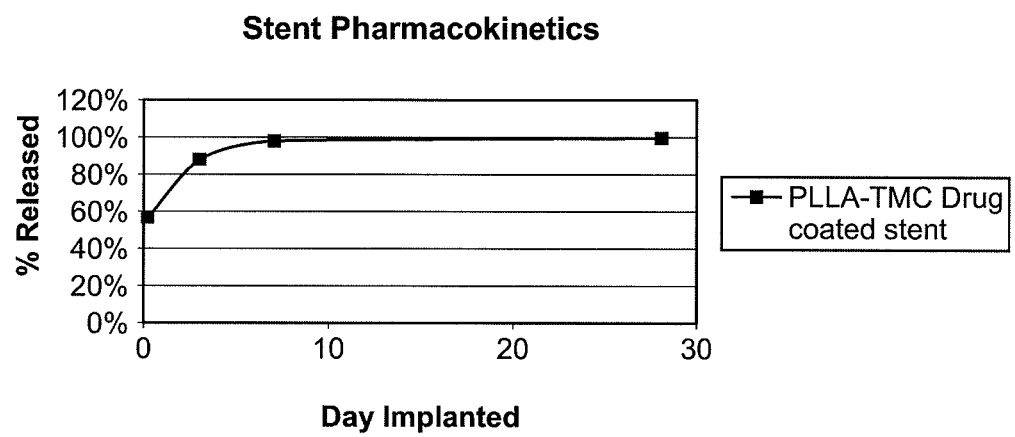
FIG. 19 is a graph illustrating the percentage of PLLA-TMC released from a coated stent in a porcine coronary artery model over time, as described in Example 14.
Figure 20:
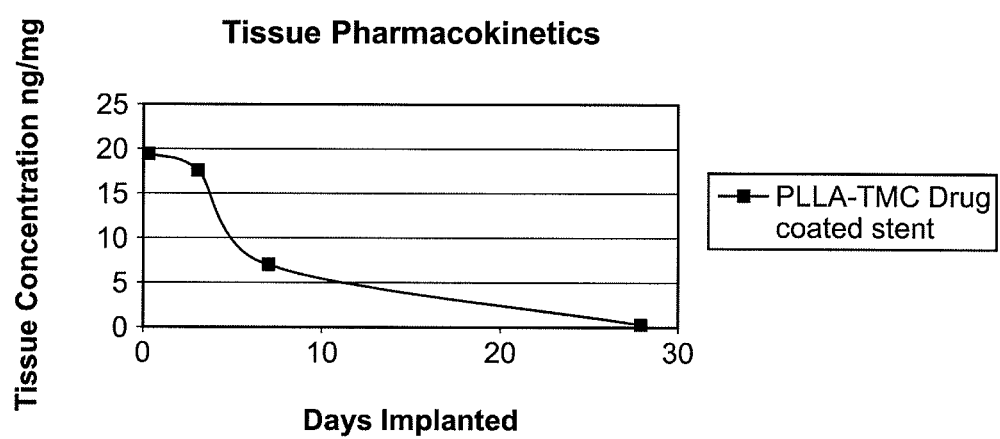
FIG. 20 is a graph illustrating the tissue concentration of PLLA-TMC over time in a porcine coronary artery model, as described in Example 12.

All animal survived to the designated end point. The stent and tissue pharmacokinetics for the PLLA-TMC drug coated stent are presented in FIGS. 19 and 20.

The PLLA-TMC drug coated stent, in this example, demonstrates the release profile of drug from the stent with approximately 90% of the drug released with in 7 days with drug tissue concentrations present over at least the same period.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A luminal prostheses comprising:
    a scaffold adapted to be radially deformed in a body lumen, said scaffold having an outer surface region and undergoing strain when the scaffold is deformed, wherein the surface region is modified to produce features having an average density in the range from 0.001 to 0.1 features per um$^2$;
    a coating deposited over the surface region, wherein the coating interact with the modified surface region to have an adherence greater than adherence in the absence of the surface modification; and
    a therapeutic agent dispersed or distributed in the coating.

2. A luminal prosthesis as in claim 1, wherein the coating softens in a physiologic environment.

3. A luminal prosthesis as in claim 2, wherein the coating comprises a polymer.

4. A luminal prosthesis as in claim 3, wherein the polymer has a glass transition temperature below physiologic temperature.

5. A luminal prosthesis as in claim 3, wherein the polymer is selected from the group consisting of poly(alkyl methacrylate) polymers, poly butyl methacrylate, poly (alkylene carbonate) polymers, polyethylene carbonate, copolymers of poly (lactide) and trimethylene carbonate, copolymers of poly (lactide) and poly (glycolide), and copolymers of poly (lactide) and polyethylene glycol.

6. A luminal prosthesis as in claim 1, wherein the features have a size in the range from 50 nm to 50 µm.

7. A luminal prosthesis as in claim 3, wherein the polymer is non-erodible in a luminal environment and has a molecular weight greater than 500 KDa.

8. A luminal prosthesis as in claim 7, wherein the polymer comprises poly-n-butylmethacrylate or another poly(alkyl methacrylate).

9. A luminal prosthesis as in claim 3, wherein the polymer is erodible in a luminal environment and has a molecular weight above 50 KDa.

10. A luminal prosthesis as in claim 9, wherein the polymer is selected from the group consisting of poly (alkylene carbonate) polymers, polyethylene carbonate, copolymers of poly (lactide) and trimethylene carbonate, copolymers of poly (lactide) and poly (glycolide), and copolymers of poly (lactide) and polyethylene glycols.

11. A luminal prosthesis as in claim 1, wherein the therapeutic agent has a concentration of at least 50% by weight based on the total weight of the coating and therapeutic agent.

12. A luminal prosthesis as in claim 1, wherein the therapeutic agent is selected from the group consisting of immunomodulators, anti-cancer agents, anti-proliferative agents, anti-inflammatory agents, antithrombotic agents, antiplatelet agents, antifungal agents, antidiabetic agents, antihyperlipidemia agents, antiangiogenic agents, angiogenic agents, antihypertensive agents, and combinations thereof.

13. A luminal prosthesis as in claim 1, wherein the scaffold is configured to have a strain of less than 50% of a peak strain in a deformed region when the scaffold undergoes radial deformation.

14. A catheter assembly comprising:
    a catheter having an expandable polymeric balloon; and
    a luminal prosthesis carried by the expandable balloon, wherein the luminal prosthesis comprises:
    a scaffold adapted to be radially deformed in a body lumen, said scaffold having an outer surface region and undergoing strain when the scaffold is deformed, wherein the surface region is modified to produce features having an average density in the range from 0.001 to 0.1 features per um$^2$;
    a coating deposited over the surface region, wherein the coating interact with the modified surface region to have an adherence greater than adherence in the absence of the surface modification; and
    a therapeutic agent dispersed or distributed in the coating.

15. A catheter assembly as in claim 14, wherein the coating softens in a physiologic environment.

16. A catheter assembly as in claim 15, wherein the coating comprises a polymer.

17. A catheter assembly as in claim 16, wherein the polymer has a glass transition temperature below physiologic temperature.

18. A catheter assembly as in claim 16, wherein the expandable balloon is composed of a polymer having a glass transition temperature below that of the coating polymer.

19. A catheter assembly as in claim 16, wherein the polymer is selected from the group consisting of poly(alkyl methacrylate) polymers, poly butyl methacrylate, poly (alkylene carbonate) polymers, polyethylene carbonate, copolymers of poly (lactide) and trimethylene carbonate, copolymers of poly (lactide) and poly (glycolide), and copolymers of poly (lactide) and polyethylene glycol.

20. A catheter assembly as in claim 14, wherein the features have a size in the range from 50 nm to 50 µm.

21. A catheter assembly as in claim 16, wherein the polymer is non-erodible in a luminal environment and has a molecular weight greater than 500 KDa.

22. A catheter assembly as in claim 21, wherein the polymer comprises poly-n-butylmethacrylate or another poly(alkyl methacrylate).

23. A catheter assembly as in claim 16, wherein the polymer is erodible in a luminal environment and has a molecular weight above 50 KDa.

24. A catheter assembly as in claim 23, wherein the polymer is selected from the group consisting of poly (alkylene carbonate) polymers, polyethylene carbonate, copolymers of poly (lactide) and trimethylene carbonate, copolymers of poly (lactide) and poly (glycolide), and copolymers of poly (lactide) and polyethylene glycols.

25. A catheter assembly as in claim 14, wherein the therapeutic agent has a concentration of at least 50% by weight based on the total weight of the coating and therapeutic agent.

26. A catheter assembly as in claim 14, wherein the therapeutic agent is selected from the group consisting of immunomodulators, anti-cancer agents, anti-proliferative agents, anti-inflammatory agents, antithrombotic agents, antiplatelet agents, antifungal agents, antidiabetic agents, antihyperlipidemia agents, antiangiogenic agents, angiogenic agents, antihypertensive agents, and combinations thereof.

27. A catheter assembly as in claim 14, wherein the scaffold is configured to have a strain of less than 50% of a peak strain in a deformed region when the scaffold undergoes radial deformation.

28. A method for coating a luminal scaffold, said method comprising:
modifying at least a portion of a surface region of the scaffold to produce surface features in the region to increase adherence of a coating, wherein the surface features have a density in the range from 0.001 to 0.1 features per um$^2$; and
coating a material over the modified surface region, wherein the material includes a therapeutic agent in the coating, and wherein the material interacts with the modified surface region to have an adherence greater than adherence in the absence of the surface modification.

29. A method as in claim 28, wherein the material softens in a physiologic environment.

30. A method as in claim 29, wherein the material comprises a polymer.

31. A method as in claim 30, wherein the polymer has a glass transition temperature below physiologic temperature.

32. A method as in claim 30, wherein the polymer is selected from the group consisting of poly(alkyl methacrylate) polymers, poly butyl methacrylate, poly (alkylene carbonate) polymers, polyethylene carbonate, copolymers of poly (lactide) and trimethylene carbonate, copolymers of poly (lactide) and poly (glycolide), and copolymers of poly (lactide) and polyethylene glycol.

33. A method as in claim 28, wherein modifying produces surface features having a size in the range from 50 nm to 50 μm.

34. A method as in claim 30, wherein the polymer is non-erodible in a luminal environment and has a molecular weight greater than 500 KDa.

35. A method as in claim 34, wherein the polymer comprises poly-n-butylmethacrylate or another poly(alkyl methacrylate).

36. A method as in claim 30, wherein the polymer is erodible in a luminal environment and has a molecular weight above 50 KDa.

37. A method as in claim 28, further comprising including a therapeutic agent in the coating.

38. A method as in claim 37, wherein the therapeutic agent is at a concentration of at least 50% by weight based on the total weight of the coating and therapeutic agent.

39. A method as in claim 37, wherein the therapeutic agent is selected from the group consisting of immunomodulators, anti-cancer agents, anti-proliferative agents, anti-inflammatory agents, antithrombotic agents, antiplatelet agents, anti-fungal agents, antidiabetic agents, antihyperlipidemia agents, antiangiogenic agents, angiogenic agents, antihypertensive agents, and combinations thereof.

40. A method as in claim 37, wherein coating comprises dissolving the therapeutic agent and the material in a solvent to form a mixture or solution and applying the mixture or solution to the modified surface region.

41. A method as in claim 40, wherein applying the mixture or solution comprises spraying, dipping, or painting.

42. A method as in claim 40, wherein the solvent has a coating solvent index value calculated by the formula:

$$IV = \frac{(ER)(VP)}{(BP)(VISC)(ST)},$$

where:
ER=evaporation rate;
VP=vapor pressure;
BP=boiling point;
VISC=viscosity; and
ST=surface tension.

43. A method as in claim 40, wherein the solvent is selected from the group consisting of dichloromethane, diethyl ether, trichlorofluoromethane, and methyl-t-butyl ether.

44. A luminal prosthesis as in claim 1, wherein the scaffold is crimped or expanded with minimal or no cracking or smearing of the coating.

45. A catheter assembly as in claim 14, wherein the scaffold is crimped or expanded with minimal or no cracking or smearing of the coating.

46. A method as in claim 28, wherein the scaffold is crimped or expanded with minimal or no cracking or smearing of the coating.

47. A luminal prosthesis as in claim 1, wherein the therapeutic agent has a concentration of at least 40% by weight based on the total weight of the coating and therapeutic agent.

48. A catheter assembly as in claim 14, wherein the therapeutic agent has a concentration of at least 40% by weight based on the total weight of the coating and therapeutic agent.

49. A method as in claim 37, wherein the therapeutic agent has a concentration of at least 40% by weight based on the total weight of the coating and therapeutic agent.

50. A luminal prosthesis as in claim 1, wherein the surface is modified by micro-blasting with a blasting media.

51. A luminal prosthesis as in claim 1, wherein the surface is modified by laser treatment.

52. A luminal prosthesis as in claim 1, wherein the surface is modified by chemical etching.

53. A catheter assembly as in claim 14, wherein the surface is modified by micro-blasting with a blasting media.

54. A catheter assembly as in claim 14, wherein the surface is modified by laser treatment.

55. A catheter assembly as in claim 14, wherein the surface is modified by chemical etching.

56. A method as in claim 28, wherein the surface is modified by micro-blasting with a blasting media.

57. A method as in claim 28, wherein the surface is modified by laser treatment.

58. A method as in claim 28, wherein the surface is modified by chemical etching.

\* \* \* \* \*